(12) United States Patent
Holloway

(10) Patent No.: US 9,402,708 B2
(45) Date of Patent: Aug. 2, 2016

(54) VASCULAR DEVICES AND METHODS WITH DISTAL PROTECTION

(71) Applicant: Covidien LP, Mansfield, MA (US)

(72) Inventor: Ken Holloway, Laguna Niguel, CA (US)

(73) Assignee: Covidien LP, Mansfield, MA (US)

( * ) Notice: Subject to any disclaimer, the term of this patent is extended or adjusted under 35 U.S.C. 154(b) by 281 days.

(21) Appl. No.: 13/950,930

(22) Filed: Jul. 25, 2013

(65) Prior Publication Data

US 2015/0032144 A1     Jan. 29, 2015

(51) Int. Cl.
*A61M 29/00* (2006.01)
*A61F 2/01* (2006.01)

(52) U.S. Cl.
CPC ......... *A61F 2/013* (2013.01); *A61F 2220/0058* (2013.01); *A61F 2230/0067* (2013.01)

(58) Field of Classification Search
CPC ..... A61F 2/01; A61F 2/013; A61F 2002/828; A61F 2/02; A61F 2002/011; A61F 2002/015; A61F 2002/016; A61F 2002/018; A61B 17/22031
USPC ................ 606/200; 623/1.11–1.143
See application file for complete search history.

(56) References Cited

U.S. PATENT DOCUMENTS

| | | | |
|---|---|---|---|
| 5,749,880 A * | 5/1998 | Banas | A61F 2/07 606/198 |
| 5,800,519 A | 9/1998 | Sandock | |
| 5,827,324 A | 10/1998 | Cassell et al. | |
| 5,941,896 A | 8/1999 | Kerr | |
| 5,947,995 A | 9/1999 | Samuels | |
| 6,231,598 B1 | 5/2001 | Berry et al. | |
| 6,254,628 B1 | 7/2001 | Wallace et al. | |
| 6,258,115 B1 | 7/2001 | Dubrul | |
| 6,402,771 B1 | 6/2002 | Palmer et al. | |
| 6,458,139 B1 | 10/2002 | Palmer et al. | |
| 6,558,405 B1 | 5/2003 | McInnes | |
| 6,991,641 B2 | 1/2006 | Diaz et al. | |
| 7,041,116 B2 | 5/2006 | Goto et al. | |
| 7,261,727 B2 | 8/2007 | Thielen | |
| 7,344,549 B2 | 3/2008 | Boyle et al. | |
| 7,344,550 B2 | 3/2008 | Carrison et al. | |

(Continued)

FOREIGN PATENT DOCUMENTS

| | | |
|---|---|---|
| CN | 1308508 A | 8/2001 |
| CN | 1663536 A | 9/2005 |

(Continued)

*Primary Examiner* — Todd E Manahan
*Assistant Examiner* — Charles Wei
(74) *Attorney, Agent, or Firm* — Mark J. Kertz, Esq.

(57) ABSTRACT

A device for treating a thrombus in a blood vessel includes a treatment section and a filter section. The treatment section can be generally cylindrical and comprise a plurality of individual filaments and individual cells, as well as a first edge and a second edge along a longitudinal axis of the device. A varying degree of overlap of the first edge and the second edge may be provided as the device transitions from a volume-reduced form to an expanded form. The filter section can be generally conical and accommodate the variable degree of overlap by providing a first section, distal to the treatment section, that has a variable degree of overlap with a non-continuous, interrupted surface. A second section, distal to the first section, has a continuous surface for providing effective filtering of debris and emboli dislodged from the thrombus during action upon the thrombus by the treatment section.

20 Claims, 9 Drawing Sheets

(56) References Cited

U.S. PATENT DOCUMENTS

| | | | |
|---|---|---|---|
| 7,749,243 | B2 | 7/2010 | Phung et al. |
| 8,029,530 | B2 | 10/2011 | Gesswein et al. |
| 2001/0025195 | A1* | 9/2001 | Shaolian .................... A61F 2/07 623/1.13 |
| 2002/0004667 | A1 | 1/2002 | Adams et al. |
| 2003/0004536 | A1 | 1/2003 | Boylan et al. |
| 2003/0004541 | A1* | 1/2003 | Linder .................... A61F 2/013 606/200 |
| 2003/0074050 | A1* | 4/2003 | Kerr ......................... A61F 2/07 623/1.13 |
| 2003/0195554 | A1 | 10/2003 | Shen et al. |
| 2004/0006370 | A1 | 1/2004 | Tsugita |
| 2004/0039412 | A1* | 2/2004 | Isshiki .................... A61F 2/013 606/200 |
| 2004/0088000 | A1* | 5/2004 | Muller .................... A61F 2/013 606/200 |
| 2004/0153117 | A1 | 8/2004 | Clubb et al. |
| 2004/0167568 | A1 | 8/2004 | Boyle et al. |
| 2004/0193208 | A1 | 9/2004 | Talpade et al. |
| 2005/0038447 | A1 | 2/2005 | Huffmaster |
| 2005/0055047 | A1 | 3/2005 | Greenhalgh |
| 2005/0131449 | A1 | 6/2005 | Salahieh et al. |
| 2005/0209678 | A1 | 9/2005 | Henkes et al. |
| 2005/0283166 | A1* | 12/2005 | Greenhalgh ......... A61B 17/221 606/113 |
| 2006/0122643 | A1 | 6/2006 | Wasicek |
| 2006/0282116 | A1 | 12/2006 | Lowe et al. |
| 2007/0060945 | A1 | 3/2007 | Gilson et al. |
| 2007/0208367 | A1 | 9/2007 | Fiorella et al. |
| 2007/0219579 | A1 | 9/2007 | Paul |
| 2007/0288054 | A1 | 12/2007 | Tanaka et al. |
| 2008/0091231 | A1 | 4/2008 | Boyle et al. |
| 2008/0208245 | A1 | 8/2008 | Hoffman |
| 2009/0105722 | A1* | 4/2009 | Fulkerson ............ A61B 17/221 606/127 |
| 2009/0240213 | A1* | 9/2009 | Miyagawa ........... A61B 17/221 604/264 |
| 2009/0240238 | A1 | 9/2009 | Grodrian et al. |
| 2010/0016946 | A1* | 1/2010 | McDermott ............. A61F 2/07 623/1.13 |
| 2010/0087908 | A1* | 4/2010 | Hilaire .................... A61F 2/013 623/1.11 |
| 2010/0106178 | A1 | 4/2010 | Obermiller et al. |
| 2010/0168786 | A1 | 7/2010 | Dower |
| 2010/0268264 | A1 | 10/2010 | Bonnette et al. |
| 2011/0060212 | A1 | 3/2011 | Slee et al. |
| 2011/0257675 | A1 | 10/2011 | Mackiewicz |
| 2011/0295304 | A1 | 12/2011 | Jonsson |
| 2012/0022634 | A1 | 1/2012 | Kusleika et al. |
| 2012/0035650 | A1 | 2/2012 | Linder et al. |
| 2012/0083868 | A1* | 4/2012 | Shrivastava ......... A61B 17/221 623/1.11 |
| 2012/0245671 | A1 | 9/2012 | Wainwright et al. |
| 2012/0265238 | A1 | 10/2012 | Hopkins et al. |
| 2012/0330346 | A1 | 12/2012 | Frimerman |
| 2013/0345739 | A1* | 12/2013 | Brady .................. A61B 17/221 606/200 |
| 2014/0088634 | A1* | 3/2014 | Sanati .................... A61F 2/013 606/200 |
| 2014/0121672 | A1* | 5/2014 | Folk ..................... A61F 2/013 606/127 |

FOREIGN PATENT DOCUMENTS

| | | |
|---|---|---|
| CN | 101147705 A | 3/2008 |
| CN | 101616639 A | 12/2009 |
| WO | WO-99/44542 A2 | 9/1999 |
| WO | WO-2012/120490 A2 | 9/2012 |

* cited by examiner

VASCULAR DEVICES AND METHODS WITH DISTAL PROTECTION

FIELD

The present disclosure relates to systems and methods for endovascular treatment of vessels in an anatomy of a patient.

BACKGROUND

During vascular surgery or endovascular treatment of vessels including thrombectomy, atherectomy, balloon angioplasty, and/or stent deployment, debris such as plaque and blood clots can move from the treatment site through a vein or artery and compromise the flow of blood at a location removed from the treatment site. In particular, various protection systems have been developed to prevent such debris from embolizing in the vessel.

SUMMARY

According to one or more implementations of the present disclosure, a device for treating a thrombus in a blood vessel includes a treatment section and a filter section. The treatment section can be generally cylindrical and comprise a plurality of individual filaments and individual cells, as well as a first edge and a second edge along a longitudinal axis of the device. A varying degree of overlap of the first edge and the second edge may be provided as the device transitions from a volume-reduced form to an expanded form. The filter section can be generally conical and accommodate the variable degree of overlap by providing a first section, distal to the treatment section, that has a variable degree of overlap with a non-continuous, interrupted surface. A second section, distal to the first section, has a continuous surface for providing effective filtering of debris and emboli dislodged from the thrombus during action upon the thrombus by the treatment section.

According to one or more implementations of the present disclosure, the filter section is provided on a distal end of the treatment section, such that they are delivered in tandem and expand together. This configuration provides timely filtration of any debris that is dislodged from the thrombus as the treatment section acts upon the thrombus. Furthermore, the integration of the filter section with the treatment section reduces complexity of the delivery components and automates expansion of the filter section according to the expansion of the treatment section.

According to one or more implementations of the present disclosure, the generally cylindrical treatment section has opposing edges along a longitudinal length thereof for a greater degree of overlap in a volume-reduced configuration and a lesser degree of overlap in an expanded configuration. The difference in structural shape between the generally cylindrical treatment section and the generally conical filter section is accommodated by the varying sections of the filter section. A first section adjacent to the treatment section provides an interrupted, non-continuous surface that provides varying degrees of overlapping between its edges, according to the configurations of the treatment section. A second section, distal to the first section, has a continuous, uninterrupted surface that effectively captures debris and emboli.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 55. The other clauses can be presented in a similar manner.

1. An expandable medical device, comprising:
a treatment section forming a cylindrical structure comprising a proximal end and a distal end; wherein the cylindrical structure has a curled mesh structure such that a seam extends along a longitudinal axis of the expandable medical device; wherein the treatment section is configured to be delivered in a volume-reduced form having overlapping edges; and wherein the cylindrical structure is configured to at least partially uncurl to allow the treatment section to assume a volume-enlarged form;
a filter section attached to the treatment section, forming a conical structure, and comprising (i) a first section, distal to the treatment section, wherein the first section is formed such that a distal seam extends along the longitudinal axis of the expandable medical device; wherein the first section is configured to have overlapping distal edges while within a catheter; and wherein the first section is configured to at least partially uncurl when released from the catheter; and (ii) a second section, distal to the first section.

2. The expandable device of clause 1, wherein the first section has a circumferentially interrupted surface and the second section has a circumferentially continuous surface.

3. The expandable device of clause 1, further comprising a tapering section proximal to the treatment section.

4. The expandable device of clause 1, wherein the treatment section comprises a plurality of cells.

5. The expandable device of clause 1, wherein the filter section further comprises a plurality of fingers, each of the fingers extending proximally from a proximal edge of the first section, through a respective cell of the treatment section, and distally back to the first section, a portion of each finger being affixed to the first section.

6. The expandable device of clause 1, wherein the second section defines an opening at a distal end of the second section.

7. The expandable device of clause 1, wherein a longitudinal length of the first section is about equal to a longitudinal length of the second section.

8. The expandable device of clause 1, wherein the treatment section, while in an expanded configuration, has a first cross-sectional dimension; the first section, while in the expanded configuration, is configured to transition, along a longitudinal length of the first section, from the first cross-sectional dimension to a second cross-sectional dimension, less than the first cross-sectional dimension; and the second section, while in the expanded configuration, transitions, along a longitudinal length of the second section, from the second cross-sectional dimension to a third cross-sectional dimension, less than the second cross-sectional dimension;

9. The expandable device of clause 1, wherein the treatment section, while in an expanded configuration, has a first cross-sectional dimension; the first section, while in the expanded configuration, transitions, along a longitudinal length of the first section, from a second cross-sectional dimension, less than the first cross-sectional dimension, to a third cross-sectional dimension, less than the second cross-sectional dimension; and the second section, while in the expanded configuration, transitions, along a longitudinal length of the second section, from the third cross-sectional dimension to a fourth cross-sectional dimension, less than the third cross-sectional dimension;

10. The expandable device of clause 1, further comprising a tapering section proximal to the treatment section.

11. The expandable device of clause 1, further comprising a wire having a proximal end and a distal end, a proximal end of the tapering section being attached to the distal end of the wire.

12. A self-expanding device for treating a thrombus, comprising:

a treatment section forming a generally cylindrical shape and comprising a seam along a longitudinal axis of the treatment section, the seam forming two edges extending generally longitudinally along the treatment section; wherein the treatment section is configured to have a generally rolled, tubular configuration with the edges of the treatment section being overlapped in the volume-reduced rolled configuration such that the treatment section has multiple layers in at least one radial direction when the treatment section is in a volume-reduced rolled configuration; wherein the treatment section is configured to self-expand from the volume-reduced rolled configuration to an expanded configuration; and a filter section attached to the treatment section, forming a generally conical configuration, and comprising (i) a first section, distal to the treatment section, having a circumferentially interrupted surface and (ii) a second section, distal to the first section, having a circumferentially continuous surface.

13. The self-expanding device of clause 12, wherein the treatment section comprises a plurality of mesh cells.

14. The self-expanding device of clause 12, wherein the filter section further comprises a plurality of fingers, each of the fingers extending proximally from a proximal edge of the first section, through a respective cell of the treatment section, and distally back to the first section, a portion of each finger being affixed to the first section.

15. The self-expanding device of clause 12, wherein the first section comprises a distal seam forming edges configured to overlap in the volume-reduced rolled configuration such that the first section has multiple layers in at least one radial direction.

16. The self-expanding device of clause 12, wherein the second section defines an opening at a distal end of the second section.

17. The self-expanding device of clause 12, wherein a longitudinal length of the first section is about equal to a longitudinal length of the second section.

18. The self-expanding device of clause 12, wherein the treatment section, while in the expanded configuration, has a first cross-sectional dimension; the first section, while in the expanded configuration, is configured to transition, along a longitudinal length of the first section, from the first cross-sectional dimension to a second cross-sectional dimension, less than the first cross-sectional dimension; and the second section, while in the expanded configuration, transitions, along a longitudinal length of the second section, from the second cross-sectional dimension to a third cross-sectional dimension, less than the second cross-sectional dimension;

19. The self-expanding device of clause 12, wherein the treatment section, while in the expanded configuration, has a first cross-sectional dimension; the first section, while in the expanded configuration, is configured to transition, along a longitudinal length of the first section, from a second cross-sectional dimension, less than the first cross-sectional dimension, to a third cross-sectional dimension, less than the second cross-sectional dimension; and the second section, while in the expanded configuration, transitions, along a longitudinal length of the second section, from the third cross-sectional dimension to a fourth cross-sectional dimension, less than the third cross-sectional dimension;

20. The self-expanding device of clause 12, further comprising a tapering section proximal to the treatment section.

21. The self-expanding device of clause 12, further comprising a wire having a proximal end and a distal end, a proximal end of the tapering section being attached to the distal end of the wire.

22. The self-expanding device of clause 12, wherein the treatment section is configured to maintain the volume reduced rolled configuration while within a catheter, and the treatment section is configured to self-expand from the volume reduced rolled configuration to the expanded configuration when released from the catheter.

23. A thrombectomy device, comprising:

a treatment section forming a cylindrical structure comprising a proximal end, a distal end, and a plurality of cells; wherein the cylindrical structure has a curled mesh structure such that a seam extends along a longitudinal axis of the expandable medical device;

a filter section attached to the treatment section, the filter section forming a conical structure, the filter section comprising a main body, a proximal edge of the main body, and a plurality of fingers, at least a portion of the main body being of a preformed unsintered polymer material, each of the plurality of fingers wrapped through a respective one of the plurality of cells of the treatment section, at least a portion of each of the plurality of fingers being sintered to the main body, at least a portion of the filter section covering a portion of an inner surface of the treatment section, at least a portion of the filter section covering a portion of an outer surface of the treatment section.

24. The thrombectomy device of clause 23, wherein a portion of the inner surface of the treatment section remains uncovered between adjacent fingers.

25. The thrombectomy device of clause 23, wherein each of the plurality of fingers is spaced apart about a circumference of the proximal edge of the first section.

26. The thrombectomy device of clause 23, wherein the treatment section is configured to be delivered in a volume-reduced form having overlapping edges; and wherein the cylindrical structure is configured to partially uncurl such that the treatment section assumes a volume-enlarged form.

27. The thrombectomy device of clause 23, wherein the filter section further comprises (i) a first section, distal to the treatment section, wherein the first section is formed such that a distal seam extends along the longitudinal axis of the expandable medical device; wherein the first section is configured to have overlapping distal edges while within a catheter; and wherein the first section is configured to partially uncurl when released from the catheter; and (ii) a second section, distal to the first section.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such as "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Distal protection devices can be separately provided and can include filters and/or occlusive devices placed distally of the treatment site. In the case of filters, emboli typically collect within or on the filter. The filter with captured emboli is typically collapsed into a recovery catheter and the catheter is withdrawn from the patient's body. Embolic protection filters typically permit the passage of blood while retaining emboli that are larger than openings provided by the filter. According to one or more implementations, a filter section may be incorporated with a treatment device for simultaneous deployment.

Figure 1:
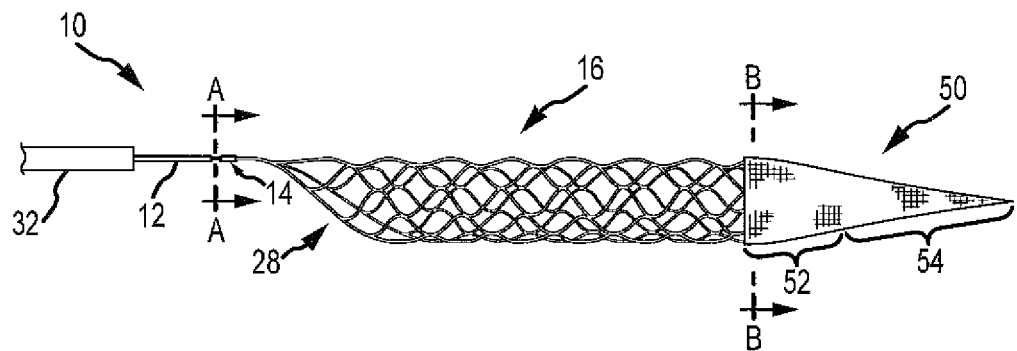
FIG. 1 shows a view of a device having a treatment section and a filter section in a curled configuration, according to one or more implementations of the present disclosure.

With reference to FIGS. 1-2, a device 10 for thrombus removal, flow restoration, and/or implantation can comprise a manipulation member in the form of a wire or guidewire 12, a (detachable or non-detachable) connection mechanism 14, a treatment section 16, and a filter section 50.

Figure 2A:
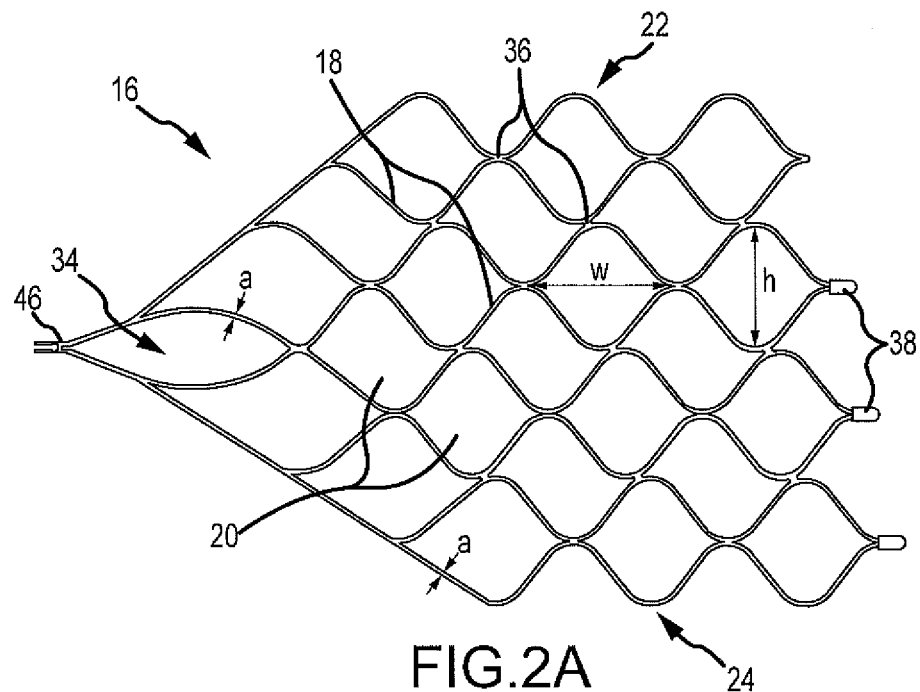
FIG. 2A shows a view of a treatment section in a flat configuration, according to one or more implementations of the present disclosure.

As shown in FIGS. 1 and 2A, the treatment section 16 can comprise a mesh structure. The mesh structure can be formed, for example, by laser cutting or etching a preformed tube, by interconnecting a multitude of filaments by braiding, weaving or laser welding, or by other suitable methods. In a preferred arrangement, the treatment section 16 is initially laser cut from a tube, such that a longitudinal slit (i.e. cut) along a length of the device is present, for example as seen in FIGS. 1-2A. In alternative embodiments, the treatment section can be formed by cutting or etching a mesh pattern on a flat sheet and then rolling the flat sheet into a generally tube-like or rolled shape. Other methods for forming the treatment section 16 are also possible.

In a preferred arrangement, the treatment section 16 can be formed from alloys having shape-memory properties, such as NITINOL®, though other materials are also possible. In one or more implementations the treatment section 16 can be subjected to a tempering treatment at temperatures customarily applied to the material so that the impressed structure is permanently established.

With continued reference to FIG. 2A, the treatment section 16 can comprise a plurality of individual filaments 18 and individual cells 20, as well as a first edge 22 and a second edge 24. The first edge 22 and second edge 24 can be formed, for example, from cutting a preformed, etched or laser-cut tube longitudinally along the length of the tube. While the first edge 22 and second edge 24 are shown as having an undulating, or sinusoidal pattern, in one or more implementations the first and second edges 22, 24 can have a straight, or linear configuration, or any other suitable configuration. Similarly, while the individual filaments 18 are shown having a particular undulating or sinusoidal pattern, in other embodiments the individual filaments 18 can have different patterns.

Figure 2B:
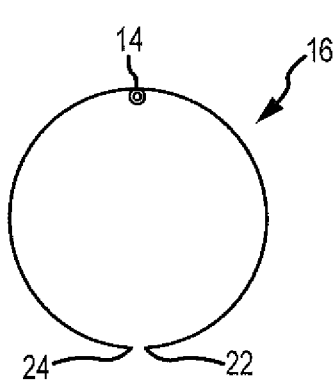
FIG. 2B shows a cross-sectional view taken at A-A of FIG. 1 showing a treatment section in a volume-expanded configuration, according to one or more implementations of the present disclosure.
Figure 2C:
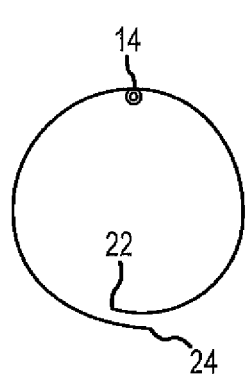
FIG. 2C shows a cross-sectional view taken at A-A of FIG. 1 showing a treatment section in a volume-expanded configuration, according to one or more implementations of the present disclosure.
Figure 2D:
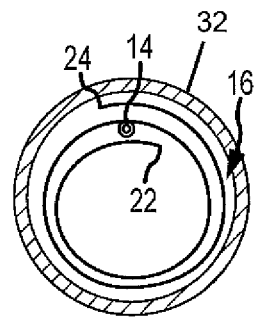
FIG. 2D shows a cross-sectional view of a treatment section in a volume-reduced configuration within a catheter, according to one or more implementations of the present disclosure.

With continued reference to FIGS. 2A, 2B, 2C, and 2D, the treatment section 16 can be curled such that edges 22 and 24 overlap one another when the treatment section 16 is in a volume-reduced form. While in a volume-reduced form, the treatment section 16, similar to a wire mesh roll or piece of paper, can be curled up such that it can be introduced into a tubular device such as a catheter or microcatheter 32 and moved within the microcatheter 32, as shown in FIG. 2D. The treatment section 16 can have a central longitudinal axis while in both a volume-reduce form and when fully or partially expanded. Upon release from the microcatheter, the curled-up treatment section 16 can spring open and attempt to assume a fully expanded shape. Upon expansion, the treatment section 16 can expand towards an inner wall of a vessel, or towards or into a thrombus occluding a vessel. The extent of any overlap of the treatment section 16 within the vessel after expansion can be governed by the vessel size and/or thrombus size. For example, in narrower vessels a greater overlap of the edges 22 and 24 can occur, as shown in FIG. 2C, whereas in wider vessels the overlap can be smaller, or even an "underlap" may occur, as shown in FIG. 2B, in which case the edges 22 and 24 are separated by an open gap or space within the vessel. As an alternative to the configuration of FIGS. 2A-2D, the edges 22 and 24 can be omitted and the treatment section 16 can be continuous where the edges would otherwise be present. For example, the stent pattern of FIG. 2A or other suitable stent pattern can be an uninterrupted, circumferentially continuous structure in the manner of a conventional laser-cut stent, without overlappable edges 22, 24 or an ability to curl as shown in FIGS. 2C-2D.

The treatment section 16 can have various lengths and diameters. In one or more implementations, the treatment section 16 can have lengths, measured proximally to distally along the longitudinal axis, ranging from 15 mm to 40 mm, though other ranges and sizes are also possible. The treatment section 16 can also have specific diameters, the diameters being measured when the treatment section 16 is fully free to expand. In one or more implementations, the treatment section 16 can have a diameter of between approximately 3 mm and 4 mm so as to be used in size 18 microcatheters (i.e. microcatheters with an inner diameter of approximately 0.21 inch). In one or more implementations the treatment section 16 can have a diameter of between approximately 5 mm and 6 mm so as to be used in size 27 microcatheters (i.e. microcatheters with an inner diameter of approximately 0.027 inch). Other ranges and values are also possible.

Figure 3A:
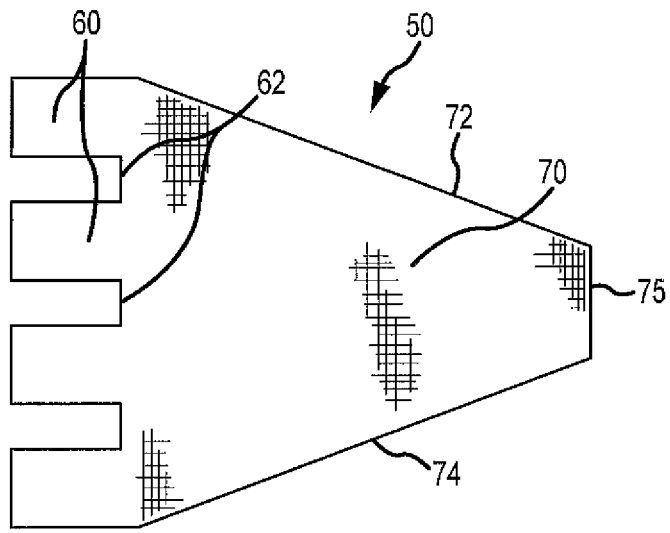
FIG. 3A shows a view of a filter section in a flat configuration, according to one or more implementations of the present disclosure.
Figure 3B:
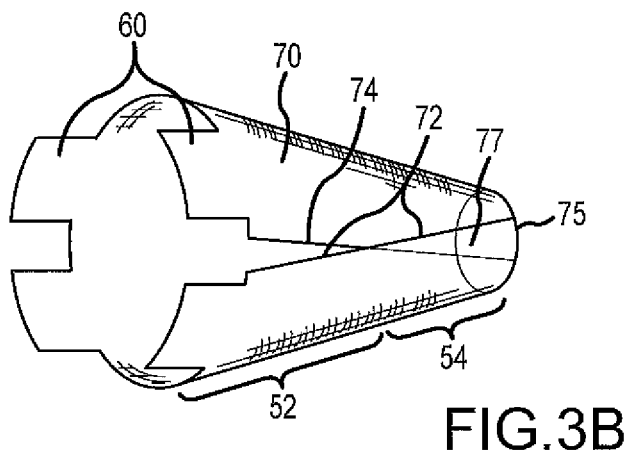
FIG. 3B shows a view of a filter section in a curled configuration, according to one or more implementations of the present disclosure.

According to one or more implementations, as shown in FIG. 1, a distal protection element such as a filter section 50 or other trap or catcher device may be provided at a distal end of the treatment section 16. As shown in FIGS. 3A and 3B, the filter section 50 may comprise, at a proximal end thereof, a plurality of proximally projecting members such as fingers 60. Each of the fingers 60 extend proximally from a proximal edge 62 of the filter section 50. The proximal edge 62 refers to a region at a proximal end of the main body 70, from which the fingers 60 extend. The proximal edge 62 or sections thereof are present between adjacent fingers 60. As shown in FIGS. 3A and 3B, the filter section 50 may comprise, at a distal end thereof, a distal edge 75. Alternatively, the filter section 50 may, at a distal end thereof, tapered to a point (as shown in FIG. 1).

According to one or more implementations, as shown in FIGS. 3A and 3B, the filter section 50 comprises a main body 70. The main body 70 comprises a material forming a sheet or film having a surface. The surface may be continuous and uninterrupted. Alternatively, the surface may be textured, cut, or perforated to provide selective perfusion of fluid and/or materials through the main body 70. For example, a laser cutting procedure may be applied to provide pores of a selected size, quantity, and distribution to the main body 70.

According to one or more implementations, as shown in FIG. 3A the filter section 50 may be cut from a sheet or film. According to one or more implementations, as shown in FIGS. 3A and 3B, the filter section 50 comprises a first edge 72 and a second edge 74 at opposing sides of the filter section 50. The first edge 72 and the second edge 74, or portions thereof, may overlap and be sealed along the length thereof.

The filter section 50 may be produced of a polymer material. For example, the filter section 50, or a portion thereof, may be of polytetrafluoroethylene ("PTFE"), expanded polytetrafluoroethylene ("ePTFE"), fluorinated ethylene propylene ("FEP"), low density polyethylene ("LDPE"), polypropylene, polyvinyl chloride ("PVC"), polydimethylsiloxane, polyethylene terephthalate ("PET") (Dacron®), polyamides (nylon), polyether urethane, polycarbonate, polysulfones, polymethyl methacrylate, poly 2-hydroxy-ethylmethacrilate (PHEMA), or combinations thereof. The polymer may provide flexibility and be readily conformable when manipulated during delivery and deployment. The polymer may also provide a coefficient of friction that allows components covered by the polymer to smoothly move past structures, such as a catheter, that constrains the components. As discussed further herein, the material for the filter section 50, a portion of the filter section 50, the fingers 60 or the main body 70 may be unsintered, e.g. an unsintered polymer such as unsintered PTFE or ePTFE. According to one or more implementations, the filter section 50 is unsintered except where fingers 60 are joined, adhered or welded to the main body 70. The term "unsintered" may include a property of a material that has not been subject to heat of a sintering process. An unsintered material may be a powder that has been preformed under pressure. A sintered material is one that has been exposed to heat to change the cross-linking structure of the material.

According to one or more implementations, the filter section 50 may be rolled or curled with at least some overlapping portions. The filter section 50 can form a generally conical structure. The phrase "generally conical" includes conical and frustoconical shapes. The phrase "generally conical" may have an appearance of being conical or frustoconical. The phrase "generally conical" may include structures that are not conical along an entire length thereof.

As shown in FIG. 3B, the first edge 72 and the second edge 74 may be brought together. The first edge 72 and the second edge 74 may be separated by a gap along a first section 52 of the filter section 50. Furthermore, the first edge 72 and the second edge 74 may cross and overlap at a second section 54 of the filter section 50 and the second section 54 may be located distal of the first section 52. In the second section 54 a region 77 of overlap may occur. As shown in FIG. 3B, the first section 52 is formed such that a distal seam extends along a longitudinal axis. The seam is formed at the region 77 of overlap. The term "seam" may describe two edges that form a region of overlap or a gap. The term "seam" does not require that two edges are fixed or attached.

The first section 52 has a circumferentially interrupted surface due to the gap between the first edge 72 and the second edge 74. The phrase "circumferentially interrupted" may describe a surface does not provide continuous coverage about an entire closed pathway about an axis. The pathway may lie within a plane transverse to the axis. The pathway about the axis need not be circular. In a compressed state, e.g. of the treatment section 16, the first edge 72 and the second edge 74 may overlap along the first section 52. However, in an expanded state, e.g. of the treatment section 16, the first edge 72 and the second edge 74 are capable of separating to provide the gap along the first section 52, as shown in FIG. 3B. As such, the first section 52 is configured to have overlapping edges 72 and 74 while the treatment section 16 is constrained in a compressed state, e.g. when the device 10 is within a catheter. The first section 52 is further configured to partially uncurl when the treatment section 16 is no longer constrained in a compressed state, e.g. when the device 10 has been released from the catheter.

The second section 54, distal to the first section 52, may have a circumferentially continuous surface in both a compressed state and an expanded state. The phrase "circumferentially continuous" may describe a surface does provide continuous coverage about an entire closed pathway about an axis. The pathway may lie within a plane transverse to the axis. The pathway about the axis need not be circular. The seam along the region 77 of overlap in the second section 54 may fix the first edge 72 relative to the second edge 74 along at least a portion of the second section 54.

According to one or more implementations, in a rolled or curled configuration, the distal edge 75 may form an opening at a distal end of the filter section 50.

Figure 3C:
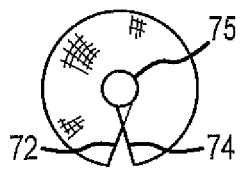
FIG. 3C shows a cross-sectional view taken at B-B of FIG. 1 showing a filter section in a volume-expanded configuration, according to one or more implementations of the present disclosure.
Figure 3D:
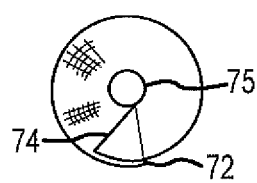
FIG. 3D shows a cross-sectional view taken at B-B of FIG. 1 showing a filter section in a volume-expanded configuration, according to one or more implementations of the present disclosure.
Figure 3E:
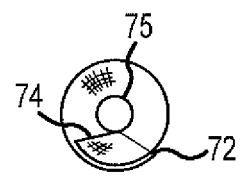
FIG. 3E shows a cross-sectional view of a filter section in a volume-reduced configuration, according to one or more implementations of the present disclosure.

With reference to FIGS. 3C, 3D, and 3E, the filter section 50 can be curled in accordance with treatment section 16, such that edges 72 and 74 overlap one another along the first section 52 when the filter section 50 is in a volume-reduced form, as shown in FIG. 3E. The filter section 50 can have a central longitudinal axis while in both a volume-reduced form and when fully or partially expanded. Upon release from the tubular device, catheter, microcatheter, etc., the curled-up first section 52 can open and attempt to assume a fully expanded shape, as shown in FIG. 3C or 3D. The extent of any overlap of the first section 52 of the filter section 50 within the vessel after expansion can be governed by the vessel size and/or the degree of expansion of the treatment section 16. Accordingly, the filter section 50 is able to accommodate the variable degree of overlap of edges 22 and 24 of the treatment section 16 while remaining attached to the treatment section 16 with the fingers 60.

As shown in FIG. 3D, the first section 52 may have a lesser degree of overlap relative to the volume-reduced form shown in FIG. 3E. For example, in narrower vessels a degree of overlap of the edges 72 and 74 can occur, as shown in FIG. 3D, whereas in wider vessels the overlap can be smaller, or even an "underlap" may occur, as shown in FIG. 3C, in which case the edges 72 and 74 are separated by an open gap or space. Both the configuration shown in FIGS. 3C and 3D have a degree of overlap less than that of the configuration shown in FIG. 3E. The degree of overlap of edges 72 and 74 along the second section 54 may remain fixed across both the volume-reduced form and the expanded form. For example, the edges 72 and 74 along the second section 54 may be fixed by adhesion or fusing, such that they do not change a degree of overlap as the filter section 50 transitions between the volume-reduced form and the expanded form.

Figure 4A:
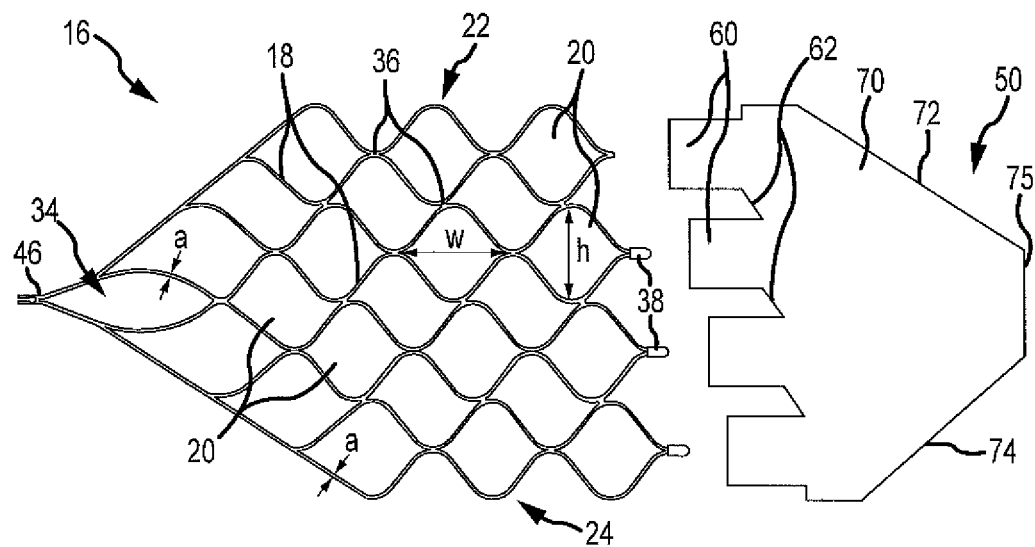
FIG. 4A shows a view of a treatment section and a filter section in a flat configuration, according to one or more implementations of the present disclosure.

According to one or more implementations, the filter section 50 is configured to connect and be attached to the treatment section 16. The treatment section 16 and the filter section 50 are shown in FIG. 4A in a flat configuration. The treatment section 16 comprises a plurality of cells 20. A row of cells 20 may be provided at a distal end of the treatment section 16. Each of the fingers 60 of the filter section 50 extend proximally from a proximal edge 62 of the filter section 50. The fingers 60 may extend from the first section 52. Each of the fingers 60 may be aligned with a corresponding cell 20 of the treatment section 16.

Figure 4B:
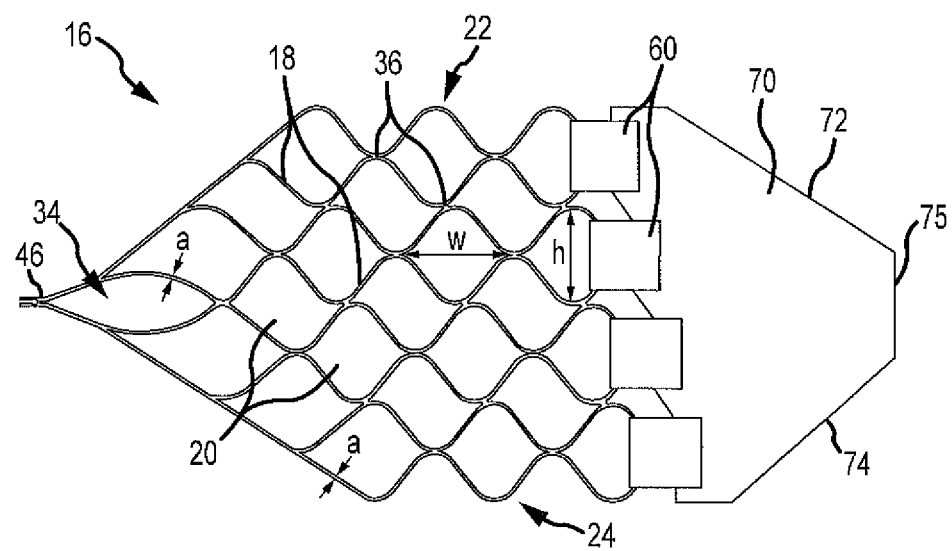
FIG. 4B shows a view of a treatment section and a filter section joined in a flat configuration, according to one or more implementations of the present disclosure.

As shown in FIG. 4B, some or each of the fingers 60 extends through a respective cell 20 of the treatment section 16 and distally back to the main body 70. Each of the fingers 60, or a portion thereof, is affixed to the main body 70. The fingers 60, or portions thereof, may be affixed at the first section 52 of the filter section 50.

Portions of the treatment section 16 are fully enveloped by the fingers 60 and the main body 70. For example, portions of filaments 18 and distal elements 38 may be fully enveloped (covered on both sides) by the fingers 60 and the main body 70, such that they are not exposed.

Figure 5A:
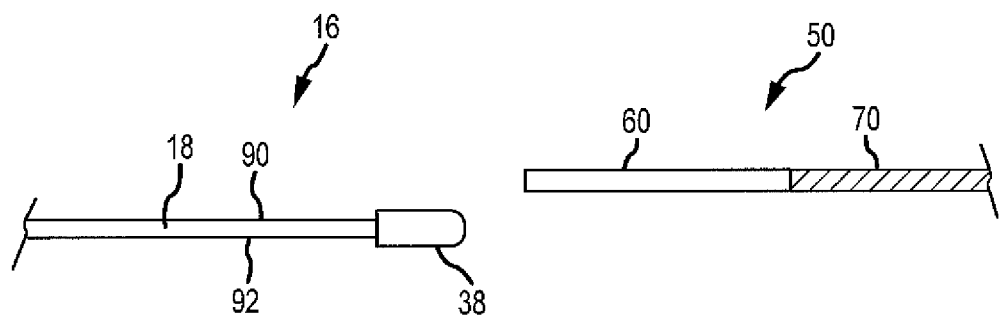
FIG. 5A shows a side view of a treatment section and a filter section, according to one or more implementations of the present disclosure.
Figure 5B:
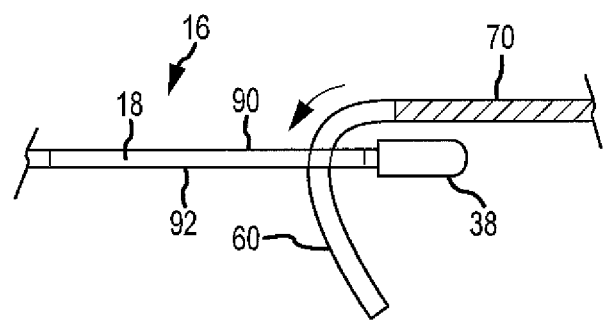
FIG. 5B shows a side view of a treatment section and a filter section, according to one or more implementations of the present disclosure.
Figure 5C:
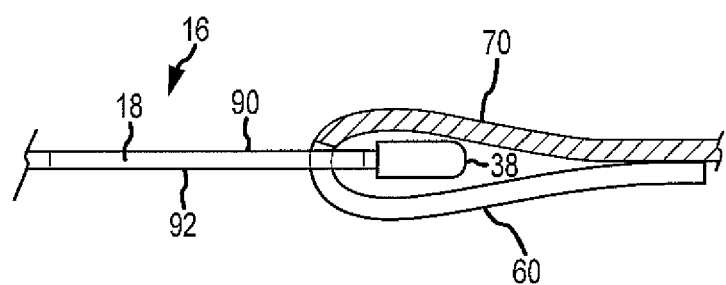
FIG. 5C shows a side view of a treatment section joined with a filter section, according to one or more implementations of the present disclosure.

FIGS. 5A-5C show further examples of the attachment of the filter section 52 to the treatment section 16. As shown in FIG. 5A, the finger(s) 60 extend from the main body 70. As shown in FIG. 5B, the fingers 60 wraps over a first surface 90 of a portion of the treatment section 16 and through a respective cell of the treatment section 16. Where a distal element 38 is present, the finger 60 may wrap around such distal element 38. As shown in FIG. 5C, the finger 60 extends distally back to the main body 70 of the filter section 50. Accordingly, the fingers 60 extends over the second surface 92 of a portion of the treatment section 16. The finger 60 can be affixed to the main body 70.

According to embodiments, the fingers 60 may be affixed to the main body 70 by welding or heat bonding. For example, the filter section 50 may be of unsintered material(s). Along regions of contact and/or overlap of the fingers 60 and the main body 70, an action may be performed to sinter at least a portion of a finger 60 to at least a portion of the main body 70.

For example, by application of heat, pressure, and/or solvents, the fingers 60 may become welded or otherwise joined or adhered to the main body 70. An example of such welding causes portions of the fingers 60 and portions of the main body 70 to sinter. Other portions of the main body 70, for example, may remain unsintered.

As shown in FIGS. 5A-5C, the filaments 18 of the treatment section 16 comprise a first surface 90 and a second surface 92. The first surface 90 may be opposite the second surface 92. For example, the first surface 90 may be the outer surface of the treatment section 16 and the second surface 92 may be the inner surface of the treatment section 16 while in a curled configuration. Alternatively, the first surface 90 may be the inner surface of the treatment section 16 and the second surface 92 may be the outer surface of the treatment section 16 while in a curled configuration.

According to one or more implementations, the first surface 90 becomes the outer surface of the treatment section 16 and the second surface 92 becomes the inner surface of the treatment section 16, when in the curled configuration. As such, the main body 70 covers the outer surface of at least a portion of the treatment section 16, and the fingers 60 cover the inner surface of at least a portion of the treatment section 16. Accordingly, an outer surface of an entire width of a distal region of the treatment section 16 may be covered by the main body 70. Where the fingers 60 are spaced apart to provide gaps between adjacent pairs of fingers, portions of the inner surface of the treatment section 16 may be exposed between adjacent pairs of fingers 60.

According to one or more implementations, the first surface 90 becomes the inner surface of the treatment section 16 and the second surface 92 becomes the outer surface of the treatment section 16, when in the curled configuration. As such, the main body 70 covers the inner surface of at least a portion of the treatment section 16, and the fingers 60 cover the outer surface of at least a portion of the treatment section 16. Accordingly, an inner surface of an entire width of a distal region of the treatment section 16 may be covered by the main body 70. Where the fingers 60 are spaced apart to provide gaps between adjacent pairs of fingers, portions of the outer surface of the treatment section 16 may be exposed between adjacent pairs of fingers 60.

Coverage of the distal region of the treatment section 16 by the main body 70 or the fingers 60 facilitates ease of delivery of the device from a catheter. For example, where the treatment section 16 has self-expanding properties, the treatment section 16 may have a tendency to expand against an inner wall of a catheter. As the device 10 is moved out of the catheter, the distal ends (e.g., distal elements 38) of the treatment section 16 are covered by the filter section 50. The filter section 50 may be of a material that provides a low coefficient of friction (e.g., polymers as disclosed herein such as PTFE, ePTFE, etc.).

Figure 6A:
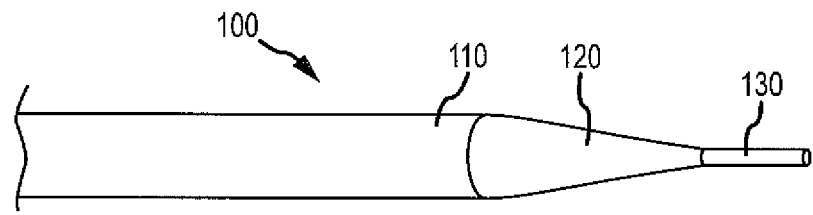
FIG. 6A shows a view of a mandrel for forming or shaping a device, according to one or more implementations of the present disclosure.
Figure 6B:
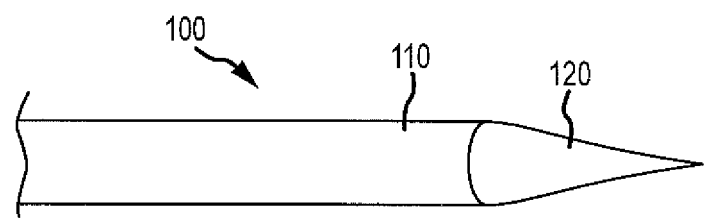
FIG. 6B shows a view of a mandrel for forming or shaping a device, according to one or more implementations of the present disclosure.

According to one or more implementations, a mandrel 100 may be provided to facilitate formation of the device 10. As shown in FIGS. 6A-6B, a first segment 110 of the mandrel 100 provides a shape for the treatment section 16 of the device 10. As shown, the first segment 110 may be generally cylindrical, such that the treatment section 16 forms a cylindrical structure. The phrase "generally cylindrical" may include structure that have an appearance of being cylindrical. The phrase "generally cylindrical" may include structures that are not cylindrical along an entire length thereof.

Figure 6C:
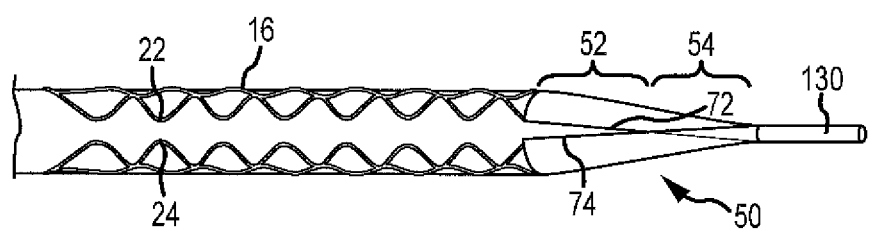
FIG. 6C shows a view of device on a mandrel, according to one or more implementations of the present disclosure.
Figure 6D:
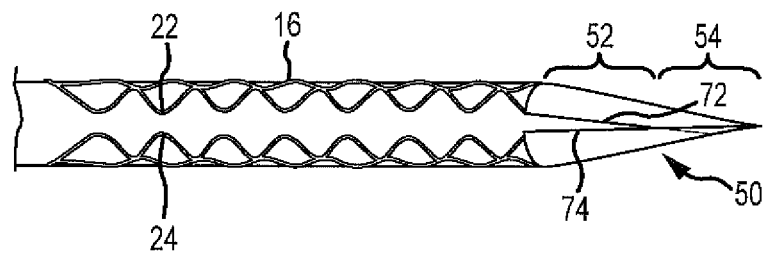
FIG. 6D shows a view of device on a mandrel, according to one or more implementations of the present disclosure.

As shown in FIGS. 6A-6B, a second segment 120 of the mandrel 100 provides a shape for the distal protection element or filter section 50 of the device 10. As shown, the second segment 120 may be generally conical, such that the filter section 50 forms a generally conical structure. For example, as shown in FIG. 6A, the second segment 120 may be frustoconical to allow an opening 91 of the filter section 50 to be defined, as shown in FIG. 6C. By further example, second segment 120 may be conical to allow the filter section 52 taper to a closed end, as shown in FIG. 6D. According to one or more implementations, at least a portion of the second segment 120 may correspond to a distal portion of the treatment section 16, such that a distal portion of the treatment section 16 tapers to a smaller cross-sectional dimension relative to that of the first segment 110.

The second segment 120 provides a surface upon which actions may be taken with respect to the filter section 50. For example, while on the mandrel 100, the fingers 60 may be welded to the main body 70 of the filter section 50. By further example, while on the mandrel 100, the first edge 72 may overlap and be welded to the second edge 74 along the second section 54 of the filter section 50 (i.e., at region 77 of overlap).

As shown in FIGS. 6A, 6C, a third segment 130 of the mandrel 100 provides a shape to define an opening 91 of filter section 50. As shown, the third segment 130 may be generally cylindrical. The transition from the second segment 120 to the third segment 130 corresponds to a region for alignment of the distal edge 75 of the filter section 50, such that the opening 91 defined by the distal edge 75 has a cross-sectional dimension about equal to that of the third segment 130.

Figure 7:
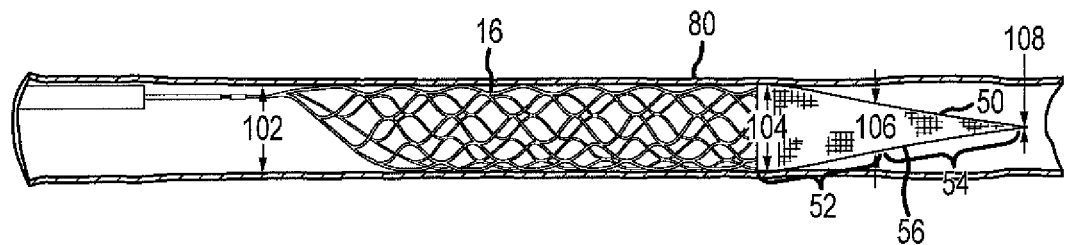
FIG. 7 shows a device expanded within a vessel, according to one or more implementations of the present disclosure.
Figure 8:
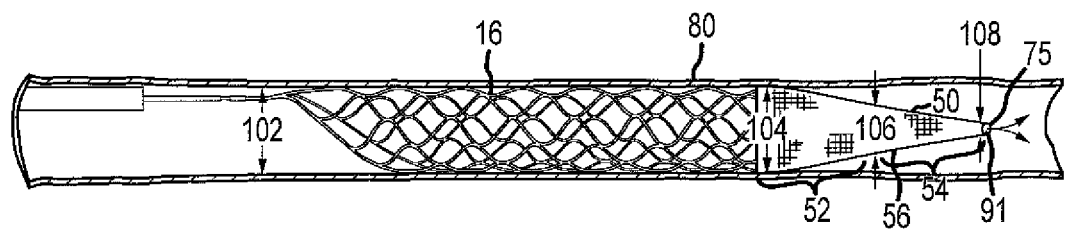
FIG. 8 shows a device expanded within a vessel, according to one or more implementations of the present disclosure.
Figure 9:
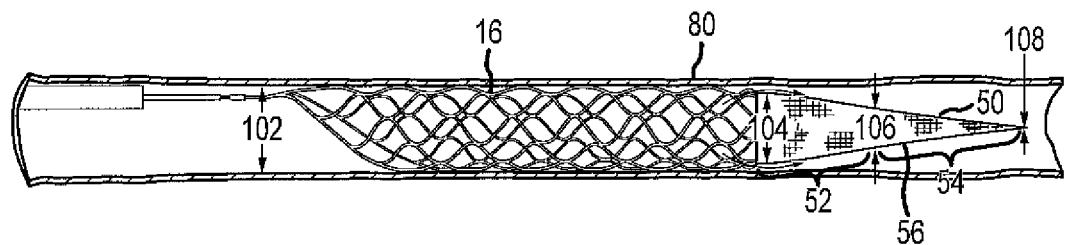
FIG. 9 shows a device expanded within a vessel, according to one or more implementations of the present disclosure.

FIGS. 7-9 illustrate various exemplary embodiments of the device 10 in expanded configurations in a vessel 80. According to one or more implementations, as shown in FIG. 7, while in the expanded configuration, the treatment section 16 has a treatment cross-sectional dimension 102. The first section 52 of the filter section 50 transitions, along a longitudinal length of the first section 52, from a first filter cross-sectional dimension 104 to a second filter cross-sectional dimension. The first filter cross-sectional dimension 104 may be about equal to the treatment cross-sectional dimension 102. The second filter cross-sectional dimension 106 may be less than the first filter cross-sectional dimension 104. The second section 54, while in the expanded configuration, transitions, along a longitudinal length of the second section 54, from the second filter cross-sectional dimension 106 to a third filter cross-sectional dimension 108. The third filter cross-sectional dimension 108 may be zero, as shown in FIG. 7. Alternatively, the third filter cross-sectional dimension 108 may be nonzero but less than the second filter cross-sectional dimension 106, as shown in FIG. 8.

According to one or more implementations, as shown in FIG. 9, while in the expanded configuration, the treatment section 16 has a treatment cross-sectional dimension 102. The first section 52 of the filter section 50 transitions, along a longitudinal length of the first section 52, from a first filter cross-sectional dimension 104 to a second filter cross-sectional dimension. The first filter cross-sectional dimension 104 is less than the treatment cross-sectional dimension 102. This configuration allows a degree of flow distally past the treatment section 16 and around and past the filter section 50. The difference between the treatment cross-sectional dimension 102 and the first filter cross-sectional dimension 104 helps determine the degree of flow and size of particles that may pass around the filter section 50. The second filter cross-sectional dimension 106 may be less than the first filter cross-sectional dimension 104. The second section 54, while in the expanded configuration, transitions, along a longitudinal length of the second section 54, from the second filter cross-sectional dimension 106 to a point or to a third filter cross-sectional dimension 108.

Figure 10:
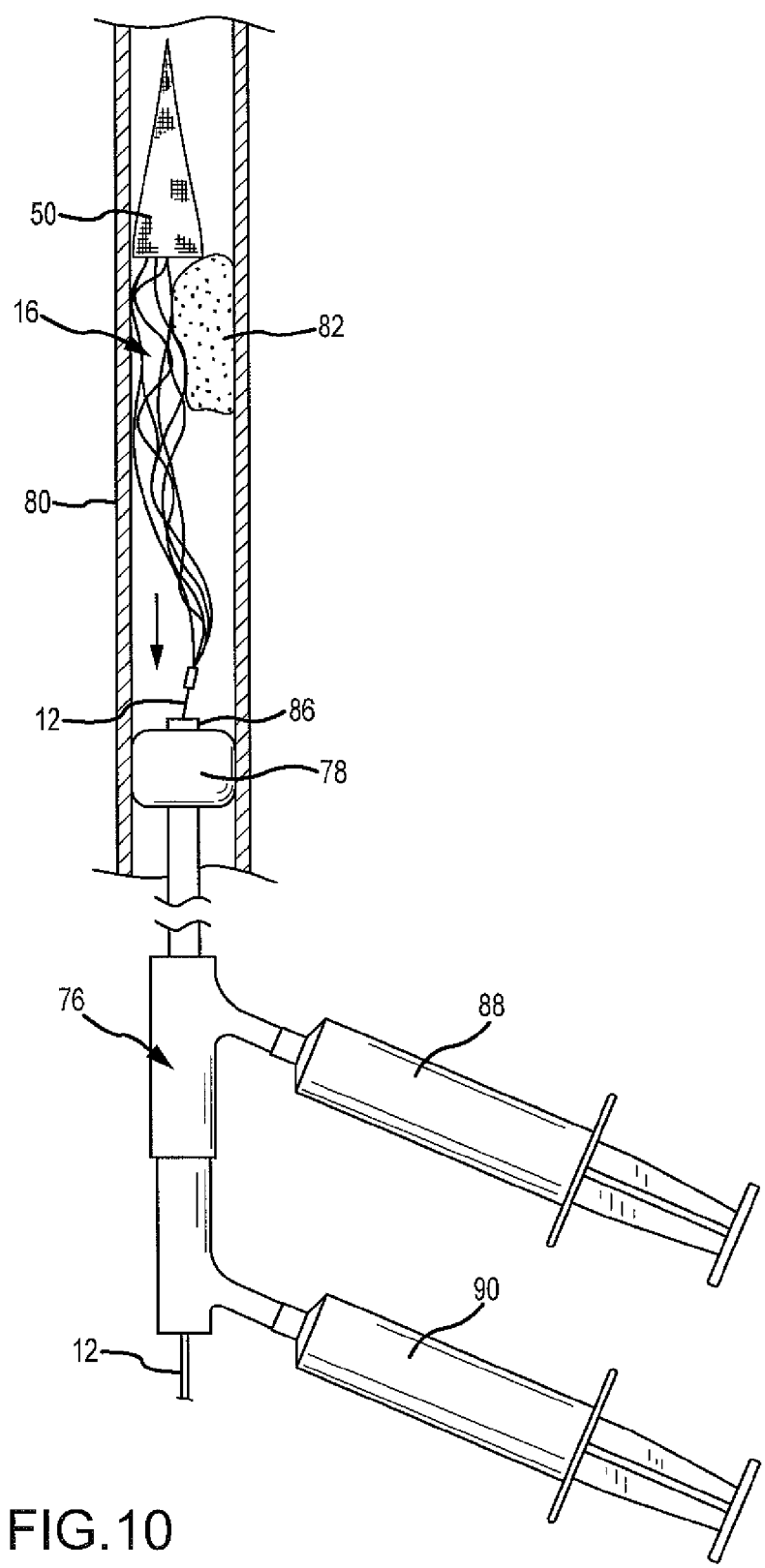
FIG. 10 shows a device and system components for treatment in a vessel, according to one or more implementations of the present disclosure.

With reference to FIGS. 10-16, and as described above, the device 10 can be used for thrombus management and removal in blood vessels such as intracranial arteries. For example, the device 10 can be used to engage and remove a thrombus in a blood vessel. By further example, the device 10 can be used to restore blood flow in a medical patient experiencing ischemic stroke due to large intracranial vessel occlusion. According to one or more implementations, the device 10 can be used in conjunction with the microcatheter 32 and a balloon guide catheter 76 as seen for example in FIGS. 10-13. The device 10 can retrieve thrombi from highly tortuous, small, and thin wall vessels. The device 10 is shown in FIG. 10 in a state of transition from a collapsed or curled configuration to an expanded configuration. The device 10 can be used to treat vessels with diameters, for example, ranging from 2.0 mm to 5.5 mm, such as the internal carotid artery, M1 and M2 segments of the middle cerebral artery, anterior cerebral artery, basilar artery and vertebral artery, though other ranges, sizes, and particular vessels are also possible.

Figure 11:
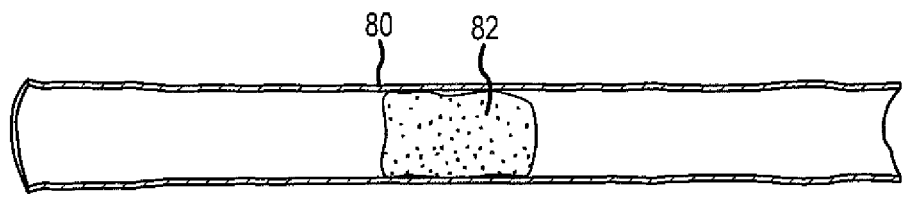
FIG. 11 shows a thrombus in a vessel, according to one or more implementations of the present disclosure.

As shown in FIG. 11, a vessel 80 may be partially or totally obstructed by a thrombus 82. During a thrombectomy procedure, the balloon guide catheter 76 can be moved through the vasculature towards a treatment area. A balloon 78, located on a distal end of the balloon guide catheter 76, can be expanded against the walls of a vessel 80. The microcatheter 32 can first be delivered through the balloon guide catheter 76 to the thrombus 82. The self-expandable member 16 can be then be delivered through the microcatheter 32. Alternatively, the device 10 can be delivered with the microcatheter 32. The device 10 can be in a volume-reduced form within the microcatheter 32. The microcatheter 32 can be advanced through the vessel 80 and placed across and/or adjacent a thrombus 82. The device 10 can be positioned across the thrombus such that a proximal portion 28 is upstream of the thrombus 82, the filter section 50 is downstream of the thrombus, and the treatment section 16 is located radially adjacent to or overlying the thrombus 82.

Figure 12:
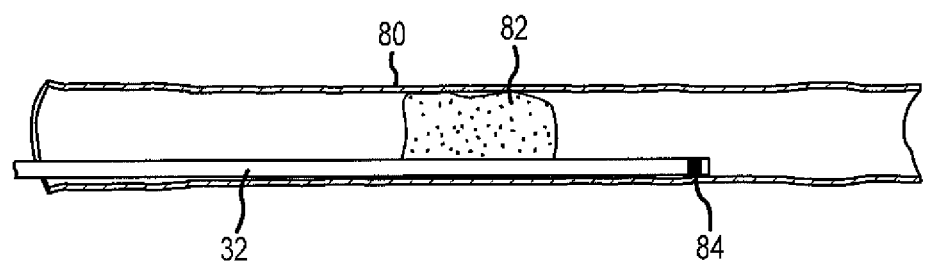
FIG. 12 shows a catheter across a thrombus in a vessel, according to one or more implementations of the present disclosure.

As shown in FIG. 12, the microcatheter 32 can be placed alongside the thrombus 82 such that a distal tip 84 of the microcatheter 32 is beyond the thrombus 82. The distal tip 84 may be from greater than about 0 mm to about 10 mm or more, or about 3 mm to about 5 mm beyond the thrombus 82, though other ranges and values are also possible. In a preferred arrangement, the treatment section 16 can be positioned such that portions of the treatment section 16 extend both proximally and distally of thrombus 82.

Figure 13:
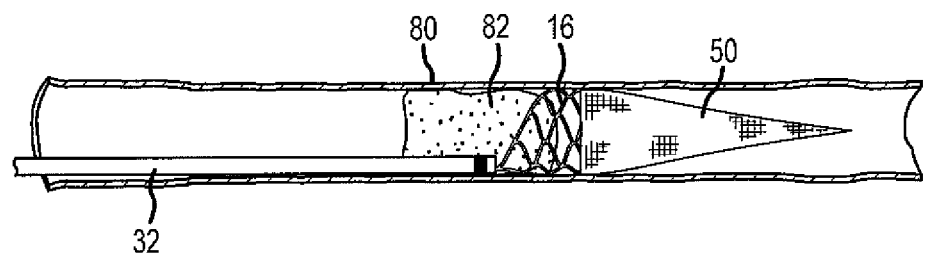
FIG. 13 shows a device partially expanded near a thrombus in a vessel, according to one or more implementations of the present disclosure.

As shown in FIG. 13, the device 10 can be held in a fixed position by holding the guidewire 12 stationary while the microcatheter 32 is withdrawn (i.e. pulled proximally). As the microcatheter is withdrawn, the treatment section 16 and filter section 50 can be released from a volume-reduced form, and can expand. According to one or more implementations, the filter section 50 may expand prior to the expansion of the treatment section 16. In an expanded configuration, the filter section 50 may provide filtering capability to capture debris dislodged during the subsequent expansion of the treatment section 16 as the microcatheter 32 is further withdrawn.

Figure 14:
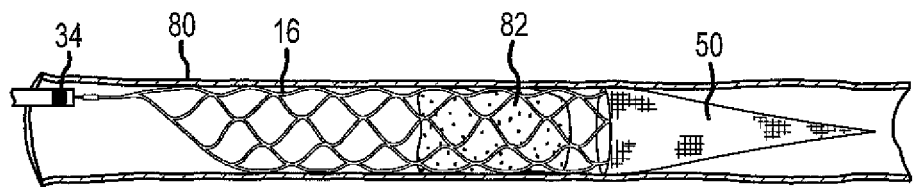
FIG. 14 shows a device expanded across a thrombus in a vessel, according to one or more implementations of the present disclosure.

As shown in FIG. 14, the treatment section 16 and filter section 50 can assume at least a portion of their unconstrained form, thereby expanding to bring at least part of the treatment section 16, and its filaments 18 and cells 20, into penetrating contact with the thrombus 82. If the position of the treatment section 16 needs to be adjusted, the guidewire 12 and/or microcatheter 32 can be moved together or individually, and if necessary, the treatment section 16 can be placed back in the microcatheter and then redeployed. The tapered proximal portion 28 can facilitate this type of repositioning.

Once deployed, the treatment section 16 can exert an outward radial force on the thrombus 82, as described above, thus reducing the cross-sectional area of the thrombus 82, forming a channel for immediately re-establishing at least partial blood flow through the blood vessel 80 past the thrombus 82, and/or loosening the thrombus from the vessel wall. In one or more implementations, for example, about 10% to about 60% of the original thrombus 82 circumference can be separated from the vessel wall after the treatment section 16 is deployed, and the ability of the thrombus 82 to hang onto the vessel wall via adhesion and friction can accordingly be reduced. In one or more implementations, the cross sectional area of the thrombus 82 can be significantly reduced by the deployed treatment section 16, resulting in a thrombus 82 having about 30% to about 95% of its original cross sectional area, but more typically about 50% to about 80% of its original cross sectional area. In one or more implementations, administration of an effective amount of a clot-busting drug, such as, for example tissue plasminogen activator (tPA), to the site of the thrombus 82 can further be applied during the blood flow restoration procedure to enhance dissolution of the thrombus 82. In one or more implementations, the open channel created by the treatment section 16 can increase the exposed surface area of the thrombus 82, thereby facilitating faster dissolution of the thrombus 82 with such clot-busting drugs.

Immediately restoring at least partial blood flow with a treatment section 16 can provide a significant benefit, and it is well established that the risk and degree of permanent neurological deficit increases rapidly with increased time from onset of symptoms to blood flow restoration. For example, immediate flow restoration can be advantageous in helping to maintain perforator patency. Thus, immediate flow restoration past the thrombus 82 can inhibit occlusion of perforator vessels nearby in the human body.

Additionally, vessels that are distal to an occluded area can often be deprived of blood flow and oxygen. Restoring blood flow in a gradual manner, through an immediate restoration of at least some partial blood flow, followed eventually by complete blood flow, can help inhibit reperfusion injury to vessels distal of the thrombus (i.e. injury caused by sudden, complete restoration of blood flow). Initial expansion of the treatment section 16 can allow the vessel to have some time to react and adapt to the changes to blood flow, pressure, stresses, and strains, and can allow the vessel to be conditioned to the onset of changes.

Figure 15:
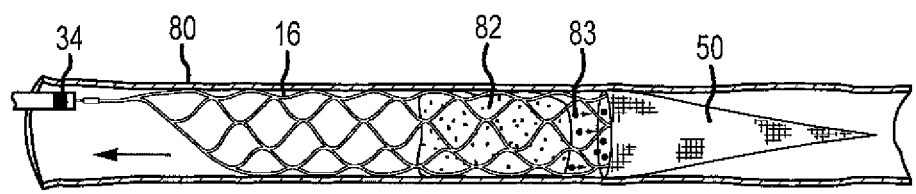
FIG. 15 shows a device with a filter section for capturing debris dislodged from a thrombus, according to one or more implementations of the present disclosure.

As shown in FIG. 15, as the treatment section 16 engages and acts upon the thrombus 82, debris 83 may be dislodged from the thrombus 82 and embolize. As the debris 83 migrate downstream, they may be captured within the filter section 50.

Figure 16:
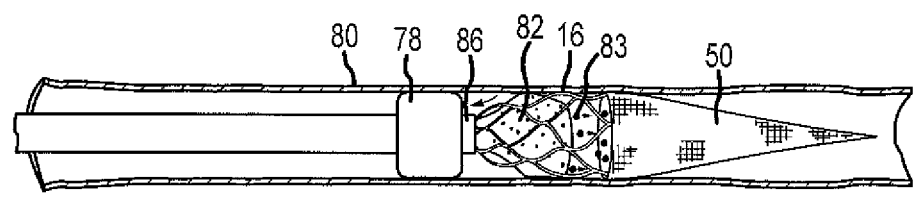
FIG. 16 shows a device and thrombus being withdrawn into a catheter, according to one or more implementations of the present disclosure.

With continued reference to FIGS. 14-16, once the treatment section 16 has engaged and captured the thrombus 82, the thrombus 82 can be removed. Prior to pulling back on the guidewire 12, the microcatheter 32 can be manipulated. For example, the microcatheter 32 can be moved forward to a predetermined point relative to the treatment section 16. Use of markers along the microcatheter 32 and/or treatment section 16 can be used to determine the relative locations of the microcatheter 32 and treatment section 16. The microcatheter 32 and treatment section 16 can then be removed together.

As the vessel size changes in diameter along a pathway traversed by the device 10, the treatment section 16 and the filter section 50 can continuously adjust by expanding or contracting to accommodate vessel size. As the treatment section 16 expands or contracts, the cells 20 can generally maintain their same shape and size, as described above, thereby inhibiting unwanted slippage or dissection of the thrombus 82. Furthermore, the filter section 50 may adapt to provide adequate coverage of the vessel 84 continual filtration of any debris 83.

With reference to FIGS. 10 and 16, during retrieval of the device 10 and thrombus 82, the initial channel created for flow restoration through or past the thrombus 82 can remain open. The balloon 78 can remain inflated to provide for maximum proximal flow control. For example, in one or more implementations the balloon 78 can ensure that there is no flow distally through the vessel from the balloon 78 towards the treatment section 16. As part of the retrieval procedure, continuous or intermittent aspiration can be employed through the balloon guide catheter 76 with vigorous aspiration when the treatment section 16 is near a distal tip 86 of the balloon guide catheter. For example, the balloon guide catheter 76 can include a syringe 88 for expanding the balloon 78, and a separate syringe 90 for aspiration. Aspiration assistance can enable flow reversal through the treatment section 16 and thrombus 82. The aspiration with flow reversal can help allow the distal vasculature to continue to have blood perfusing through the vessels during the retrieval process, and can inhibit the possibility of distal emboli. There can be an advantage to having blood flow across the treatment section 16, the filter section 50, and the thrombus 82 with the potential of natural lysing of blood and increased surface area for thrombus dissolving medicines, if they are provided. The aspiration with flow reversal can also assist in the thrombus retrieval process by aiding in the removal of the thrombus 82. The flow can be directed towards the lumen of the balloon guide catheter 76 due to the aspiration. The treatment section 16 and thrombus 82 can thus be assisted by the flow to enter the lumen of the balloon guide catheter 76. In one or more implementations, if withdrawal into the balloon guide catheter 76 is difficult for any reason during aspiration, the balloon 78 can be deflated, and the balloon guide catheter 76, microcatheter 32, and device 10 as a unit can be withdrawn simultaneously while maintaining aspiration.

Additionally, and as described above, the device 10 can be used as an implantable member (e.g. stent). For example, the guidewire 12, connection mechanism 14, treatment section 16, and filter 50 can be delivered through a microcatheter 32 to a treatment site such as a stenosis or aneurysm. Similar to the method described above, the microcatheter can be withdrawn, and the device 10 can expand against a vessel wall. Similar to use as a flow restoration device, if necessary the device 10 can be repositioned if it is not placed correctly on a first attempt. Once the device 10 is in a desired location at the treatment site, the device 10 can then be detached from the guidewire 12 and be used as an implantable member.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. An expandable medical device, comprising:
   a treatment section forming a cylindrical structure comprising a proximal end and a distal end; wherein the cylindrical structure has a curled mesh structure such that a seam extends along a longitudinal axis of the expandable medical device; wherein the treatment section is configured to be delivered in a volume-reduced form having overlapping edges; and wherein the cylindrical structure is configured to at least partially uncurl to allow the treatment section to assume a volume-enlarged form;

a filter section attached to the treatment section, forming a conical structure, and comprising (i) a first section, distal to the treatment section, wherein the first section is configured to have overlapping first edges while the treatment section is in the volume-reduced form, and wherein the first edges are configured not to overlap while the treatment section is in the volume-enlarged form; and (ii) a second section, distal to the first section, wherein the second section is configured to have overlapping second edges while the treatment section is in the volume-reduced form and while the treatment section is in the volume-enlarged form.

2. The expandable device of claim 1, wherein the first section has a circumferentially interrupted surface and the second section has a circumferentially continuous surface.

3. The expandable device of claim 1, further comprising a tapering section proximal to the treatment section.

4. The expandable device of claim 1, wherein the treatment section comprises a plurality of cells.

5. The expandable device of claim 1, wherein the filter section further comprises a plurality of fingers, each of the fingers extending proximally from a proximal edge of the first section, through a respective cell of the treatment section, and distally back to the first section, a portion of each finger being affixed to the first section.

6. The expandable device of claim 1, wherein the second section defines an opening at a distal end of the second section.

7. The expandable device of claim 1, wherein the treatment section, while in an expanded configuration, has a first cross-sectional dimension; the first section, while in the expanded configuration, is configured to transition, along a longitudinal length of the first section, from the first cross-sectional dimension to a second cross-sectional dimension, less than the first cross-sectional dimension; and the second section, while in the expanded configuration, transitions, along a longitudinal length of the second section, from the second cross-sectional dimension to a third cross-sectional dimension, less than the second cross-sectional dimension.

8. The expandable device of claim 1, wherein the treatment section, while in an expanded configuration, has a first cross-sectional dimension; the first section, while in the expanded configuration, transitions, along a longitudinal length of the first section, from a second cross-sectional dimension, less than the first cross-sectional dimension, to a third cross-sectional dimension, less than the second cross-sectional dimension; and the second section, while in the expanded configuration, transitions, along a longitudinal length of the second section, from the third cross-sectional dimension to a fourth cross-sectional dimension, less than the third cross-sectional dimension.

9. A self-expanding device for treating a thrombus, comprising:

a treatment section forming a generally cylindrical shape and comprising a seam along a longitudinal axis of the treatment section, the seam forming two edges extending generally longitudinally along the treatment section; wherein the treatment section is configured to have a generally rolled, tubular configuration with the edges of the treatment section being overlapped in a volume-reduced rolled configuration such that the treatment section has multiple layers in at least one radial direction when the treatment section is in the volume-reduced rolled configuration; wherein the treatment section is configured to self-expand from the volume-reduced rolled configuration to an expanded configuration; and a filter section attached to the treatment section, forming a generally conical configuration, and comprising (i) a first section, distal to the treatment section, having a circumferentially continuous surface while the treatment section is in the volume-reduced rolled configuration and a circumferentially interrupted surface while the treatment section is in the expanded configuration and (ii) a second section, distal to the first section, having a circumferentially continuous surface while the treatment section is in the volume-reduced rolled configuration and while the treatment section is in the expanded configuration.

10. The self-expanding device of claim 9, wherein the treatment section comprises a plurality of mesh cells.

11. The self-expanding device of claim 9, wherein the filter section further comprises a plurality of fingers, each of the fingers extending proximally from a proximal edge of the first section, through a respective cell of the treatment section, and distally back to the first section, a portion of each finger being affixed to the first section.

12. The self-expanding device of claim 9, wherein the first section comprises a distal seam forming edges configured to overlap in the volume-reduced rolled configuration such that the first section has multiple layers in at least one radial direction.

13. The self-expanding device of claim 9, wherein the second section defines an opening at a distal end of the second section.

14. The self-expanding device of claim 9, wherein the treatment section, while in the expanded configuration, has a first cross-sectional dimension; the first section, while in the expanded configuration, is configured to transition, along a longitudinal length of the first section, from the first cross-sectional dimension to a second cross-sectional dimension, less than the first cross-sectional dimension; and the second section, while in the expanded configuration, transitions, along a longitudinal length of the second section, from the second cross-sectional dimension to a third cross-sectional dimension, less than the second cross-sectional dimension.

15. The self-expanding device of claim 9, wherein the treatment section, while in the expanded configuration, has a first cross-sectional dimension; the first section, while in the expanded configuration, is configured to transition, along a longitudinal length of the first section, from a second cross-sectional dimension, less than the first cross-sectional dimension, to a third cross-sectional dimension, less than the second cross-sectional dimension; and the second section, while in the expanded configuration, transitions, along a longitudinal length of the second section, from the third cross-sectional dimension to a fourth cross-sectional dimension, less than the third cross-sectional dimension.

16. The self-expanding device of claim 9, wherein the treatment section is configured to maintain the volume-reduced rolled configuration while within a catheter, and the treatment section is configured to self-expand from the volume-reduced rolled configuration to the expanded configuration when released from the catheter.

17. A thrombectomy device, comprising:

a treatment section forming a cylindrical structure comprising a proximal end, a distal end, and a plurality of cells; wherein the cylindrical structure has a curled mesh structure such that a seam extends along a longitudinal axis of the thrombectomy device, wherein the treatment section is configured to at least partially uncurl from a volume-reduced form to a volume-enlarged form;
a filter section attached to the treatment section, the filter section forming a conical structure, the filter section comprising a main body, a proximal edge of the main body, and a plurality of fingers, at least a portion of the main body being of a preformed unsintered polymer material, each of the plurality of fingers wrapped through a respective one of the plurality of cells of the treatment section, at least a portion of each of the plurality of fingers being sintered to the main body, at least a portion of the filter section covering a portion of an inner surface of the treatment section, at least a portion of the filter section covering a portion of an outer surface of the treatment section, the main body comprising (i) a first section configured to have overlapping first edges while the treatment section is in the volume-reduced form, and wherein the first edges are configured not to overlap while the treatment section is in the volume-enlarged form; and (ii) a second section, distal to the first section, wherein the second section is configured to have overlapping second edges while the treatment section is in the volume-reduced form and while the treatment section is in the volume-enlarged form.

18. The thrombectomy device of claim 17, wherein a portion of the inner surface of the treatment section remains uncovered between adjacent fingers.

19. The thrombectomy device of claim 17, wherein each of the plurality of fingers is spaced apart about a circumference of the proximal edge of the first section.

20. The thrombectomy device of claim 17, wherein the treatment section is configured to be delivered in the volume-reduced form having overlapping edges.

* * * * *